US007754253B2

(12) United States Patent
LeLouarn

(10) Patent No.: US 7,754,253 B2
(45) Date of Patent: Jul. 13, 2010

(54) BOTULINUM TOXIN FOR THE TREATMENT OF REDUCTION OF HAIR GROWTH

(75) Inventor: Claude LeLouarn, Paris (FR)

(73) Assignee: Ipsen Pharma S.A.S., Paris (FR)

( * ) Notice: Subject to any disclaimer, the term of this patent is extended or adjusted under 35 U.S.C. 154(b) by 0 days.

(21) Appl. No.: 10/591,582

(22) PCT Filed: Mar. 2, 2005

(86) PCT No.: PCT/FR2005/000495

§ 371 (c)(1),
(2), (4) Date: May 23, 2007

(87) PCT Pub. No.: WO2005/087258

PCT Pub. Date: Sep. 22, 2005

(65) Prior Publication Data
US 2007/0292546 A1    Dec. 20, 2007

(30) Foreign Application Priority Data
Mar. 4, 2004    (EP)    .................................. 04290582

(51) Int. Cl.
*A61K 35/00*    (2006.01)
(52) U.S. Cl. .................................................... 424/780
(58) Field of Classification Search ........................ None
See application file for complete search history.

(56) References Cited

U.S. PATENT DOCUMENTS 5,562,907 A * 10/1996 Arnon
6,299,893 B1 * 10/2001 Schwartz et al.
2002/0028765 A1 * 3/2002 Maurer
2002/0177545 A1 * 11/2002 Donovan

FOREIGN PATENT DOCUMENTS

FR    2 813 532 A    3/2002

OTHER PUBLICATIONS http://www.hypertrichosis.com/hypertrichosis-biology/what-hypertrichosis.shtml. "What is Hypertrichosis?". Downloaded Nov. 6, 2007.*
http://www.csmc.edu/pdf/HIRSUTISM9112002.pdf; Sep. 200. Cedars-Sinai Medical Center: Hirsutism. Downloaded Nov. 6, 2007.*
Kinkelin, I et al. British Journal of Dermatology (2000); 143: 824-827. Effective treatment of frontal hyperhidrosis with botulinum A.*
Andreyko, JL et al. Journal of Clinical Endocrinology & Metabolism (1986); 63: 854-859. Treatment of hirsutism with a gonadrotopin-releasing hormone agonist (nafarelin). Abstract.*
http://www.wdxcyber.com/ninfer07.htm. Jelovsek, FR. Evaluation of Excessive Hair Growth (Hirsutism). Downloaded from the world-wide web on Aug. 2, 2009.*
http://medical-dictionary.thefreedictionary.com/Downy+hair. The Free Dictionary: "lanugo". Downloaded from the world-wide web on Aug. 2, 2009.*
http:/Iwww.csmc.edulpdf1HIRSUTISM9112002.pdf; Sep. 200. Cedars-Sinai Medical Center: Hirsutism. Downloaded Nov. 6, 2007.*
Asada-Kubota M: "Inhibition of Hair Growth by Subcutaneous Injection of a Sympathetic Neurotoxin, 6-Hydroxydopamine in Neonatal Mice." Anatomy and Embryology, Springer, vol. 191, No. 5, May 1995, pp. 407-414, XP000861802; ISSN: 0340-2061.
Le Louarn C: "'The Plastic Surgeon and the Prevention of Facial Aging Process!'" Annales de Chirurgie Plastique et Esthetique. Oct. 2003, vol. 48, No. 5, Oct. 2003, pp. 346-349, XP002287709, ISSN: 0294-1260.
Azziz Ricardo: "The Evaluation and Management of Hirsutism." Obstetrics and Gynecology, vol. 101, No. 5, Part 1, May 2003, pp. 995-1007, XP002287710, ISSN: 0029-7844.
Wendelin Daniel S. et al.: "Hypertrichosis." Journal of the American Academy of Dermatology. Feb. 2003, vol. 48, No. 2, Feb. 2003, pp. 161-179, qui, XP002287711, ISSN: 0190-9622.

* cited by examiner

*Primary Examiner*—Michele Flood
(74) *Attorney, Agent, or Firm*—Hunton & Williams LLP

(57) ABSTRACT

The use of botulinum toxin for preparing a drug for preventing hair growth is disclosed. A cosmetic method for preventing hair growth is also disclosed.

18 Claims, No Drawings

BOTULINUM TOXIN FOR THE TREATMENT OF REDUCTION OF HAIR GROWTH

FIELD OF INVENTION

A subject of the present invention is the use of botulinum toxin for the preparation of a medicament intended to prevent hair growth. It also relates to a cosmetic method for the prevention of hair growth.

For people who have hypertrichosis or women with hirsutism, hair growth represents a great embarrassment. Moreover, for some people, in particular for women, the presence of hair on certain parts of the body is however considered to be particularly unsightly.

There is therefore a need for a method which allows for the limiting, in an effective way and without adverse drug reactions, of hair regrowth in the people mentioned previously.

The subject of the present invention is to provide a particularly effective solution without side effects.

BACKGROUND OF INVENTION

Botulinum toxin, in particular botulinum toxin of type A (Dysport® marketed by Ipsen or Botox® marketed by Allergan), has been used since the 80s in humans for the treatment of diverse and varied diseases/disorders. Among the diseases/disorders which can be treated with botulinum toxin, neuromuscular disorders (for example blepharospasm, adult or child spasticity or also torticollis), migraines, pain in general, urological disorders (for example benign prostatic hyperplasia, urinary retention or incontinence), diabetes, hyperhidrosis (or excessive perspiration), hypersalivation or even wrinkles can be mentioned among others.

BRIEF SUMMARY OF THE INVENTION

According to the invention, botulinum toxin is used to prevent hair growth in a person with hypertrichosis or in a patient suffering from hirsutism, or in people who are healthy or optionally have hypertrichosis who want a cosmetic treatment in order to prevent hair growth.

The invention therefore relates in particular to the use of botulinum toxin for the preparation of a medicament intended to prevent hair growth in a person with hypertrichosis or in a patient suffering from hirsutism.

The invention also relates to a cosmetic treatment method intended to prevent hair growth in a person wanting such a treatment, said method comprising the administration, to the area to be treated, of a pharmaceutical composition containing botulinum toxin in an effective quantity.

One of the main advantages of the invention resides in the relatively long-lasting effect obtained using botulinum toxin. Thus, this effect generally lasts for at least 3 or 4 months after the administration of the botulinum toxin (or more in some patients).

DETAILED DESCRIPTION OF THE INVENTION

The botulinum toxin used for the preparation of a medicament according to the invention is chosen from the botulinum toxins of type A (including in particular A1 and A2), B, C (including in particular C1 and C2), D, E, F and G. Preferably, it is chosen from the botulinum toxins of type A, B and F. Yet more preferably, it is chosen from the botulinum toxins of type A and B; in particular, it is the botulinum toxin of type A (and more particularly botulinum toxin of type A1).

Moreover, the botulinum toxin used for the preparation of a medicament according to the invention can be in the form of a complex comprising botulinum toxin and other proteins or in free form (i.e. free of any protein which forms a complex with it).

According to the invention, the prepared medicament can in particular be a lyophilized powder comprising botulinum toxin (in which case the doctor will reconstitute the solution with water or an aqueous saline solution before injecting it into the patient) or also an injectionable solution comprising said toxin.

The above considerations relating to the botulinum toxin used for the preparation of a medicament according to the invention and the medicament obtained are applicable mutatis mutandis to the botulinum toxin used for the cosmetic treatment method according to the invention and to the cosmetic agent used for the implementation of said cosmetic treatment method.

The medicament prepared according to the invention is intended to be administered, for example by injection, to the areas of the patient effected by excessive hair growth which have been chosen by the attending doctor, preferably after these areas have been shaved. Preferably, these areas are chosen from the group constituted by the face, the thorax, the abdomen, the gluteal region, the genitocrural region, the legs and the arms.

For cosmetic treatment, a liquid or semi-liquid composition or also a gel comprising botulinum toxin could, for example, be injected into the areas where the epilation has taken place or will take place later. Alternatively, a patch containing botulinum toxin can be applied, or a cream containing botulinum toxin may be spread, on the area to be treated.

Preferably, the area of the body to which the cosmetic treatment method is applied is chosen from the group constituted by the torso (for example the breasts), the legs (for example the thighs), the arms, the armpits and the face (for example the supraorbital ridge, the area situated between the lips and the nose [i.e. the white upper lip], the chin or the cheeks).

As regards the administration route of the medicament or of the cosmetic treatment according to the invention, a person skilled in the art can envisage any suitable administration route; however, said administration route is preferably chosen so that the botulinum toxin, once administered, is essentially spread on the epidermis of the areas to be treated.

Of course, the uses according to the invention can also be employed to carry out therapeutic or cosmetic treatments intended for pets whose hair growth is excessive or bothers their owner.

The dose of botulinum toxin to be provided according to the present invention will vary according to the age and the body weight of the subject to be treated as well as the condition of the latter, and the attending doctor or veterinarian will make the final decision. Such a quantity determined by the attending doctor or veterinarian is called here "therapeutically effective quantity".

By way of example, for the botulinum toxin of type A1, the administration dose envisaged for a medicament according to the invention can be from 0.05 to 1 $LD_{50}$ units of botulinum toxin of type A1 per $cm^2$ of skin to be treated, preferably from 0.1 to 0.5 $LD_{50}$ units of botulinum toxin of type A1 per $cm^2$ of skin to be treated and more preferably from 0.2 to 0.4 $LD_{50}$ units of botulinum toxin of type A1 per $cm^2$ of skin to be treated (for example approximately 0.3 $LD_{50}$ units of botulinum toxin of type A1 per $cm^2$ of skin to be treated). For the botulinum toxins of other types, a person skilled in the art will change the necessary dose insofar as he knows the relative therapeutic activity of each of these botulinum toxins in relation to the botulinum toxin of type A1. The $LD_{50}$ units are currently used by the doctor using botulinum toxin; an $LD_{50}$ unit of botulinum toxin corresponds to the equivalent toxin dose killing 50% of a group of 18 to 20 female Swiss-Webster mice weighing approximately 20 grams each.

The term "approximately" refers to an interval around the value considered. As it is used in the present application, "approximately X" signifies an interval of X minus 10% of X to X plus 10% of X, and preferably an interval of X minus 5% of X to X plus 5% of X.

Unless otherwise defined, all the technical and scientific terms used here have the same meaning as that usually understood by a specialist in the field to which this invention belongs. Similarly, all the publications, patent applications, all the patents and all other references mentioned here are incorporated by way of reference.

The following example is presented in order to illustrate the above procedures and should in no event be considered as a limit to the scope of the invention.

EXAMPLE

A patient of 39 years of age wants to reduce the downy hairs on their upper lip. A solution containing 3 units of Botox® (a product marketed by Allergan France; the solution is prepared according to the manufacturer's instructions) is injected into the epidermis of this patient, at several points situated just above the red of their upper lip, the 3 units being spread evenly over the treated area. In the follow-up, 4 months later, the patient clearly presents less downy hair on the upper lip.

The invention claimed is:

1. A method for reducing downy hair growth in a female patient from comprising injecting a therapeutically effective amount of botulinum toxin type A to the area situated between the lips and the nose of said patient.

2. The method for reducing hair growth of claim 1, wherein the method comprises shaving the area between the lips and the nose of the patient prior to administering the botulinum toxin.

3. The method of claim 1, wherein the effective amount is from 0.05 to 1 $LD_{50}$ units of botulinum toxin type A per $cm^2$ of skin.

4. The method of claim 3, wherein the effective amount is from 0.1 to 0.5 $LD_{50}$ units of botulinum toxin type A per $cm^2$ of skin.

5. The method of claim 4, wherein the effective amount is from 0.2 to 0.4 $LD_{50}$ units of botulinum toxin type A per $cm^2$ of skin.

6. The method of claim 5, wherein the effective amount is 0.3 $LD_{50}$ units of botulinum toxin type A per $cm^2$ of skin.

7. The method of claim 1, wherein the botulinum toxin type A is A1.

8. The method of claim 1, wherein the botulinum toxin type A is A2.

9. A method for reducing downy hair growth in a female patient comprising shaving an area of skin on the patient followed by injecting a therapeutically effective amount of botulinum toxin type A to the shaved area.

10. The method of claim 9, wherein the area of skin is the face, torso, abdomen, gluteal region, armpits, genitocrural region, legs, or arms.

11. The method of claim 10, wherein the area of the torso is the breasts.

12. The method of claim 9, wherein the area of the face is the area situated between the lips and the nose, chin, supraorbital ridge, or cheeks.

13. The method of claim 9, wherein the effective amount is from 0.05 to 1 $LD_{50}$ units of botulinum toxin type A per $cm^2$ of skin.

14. The method of claim 13, wherein the effective amount is from 0.1 to 0.5 $LD_{50}$ units of botulinum toxin type A per $cm^2$ of skin.

15. The method of claim 14, wherein the effective amount is from 0.2 to 0.4 $LD_{50}$ units of botulinum toxin type A per $cm^2$ of skin.

16. The method of claim 15, wherein the effective amount is 0.3 $LD_{50}$ units of botulinum toxin type A per $cm^2$ of skin.

17. The method of claim 9, wherein the botulinum toxin type A is A1.

18. The method of claim 9, wherein the botulinum toxin type A is A2.

* * * * *